US009555149B2

(12) United States Patent
Shinohara et al.

(10) Patent No.: US 9,555,149 B2
(45) Date of Patent: Jan. 31, 2017

(54) MEDICAL MATERIAL EMPLOYING CARBOXYMETHYL CELLULOSE

(71) Applicant: ASAHI KASEI FIBERS CORPORATION, Osaka (JP)

(72) Inventors: Mika Shinohara, Tokyo (JP); Kyoko Machioka, Tokyo (JP); Masaya Fuke, Tokyo (JP)

(73) Assignee: ASAHI KASEI FIBERS CORPORATION, Osaka-Shi (JP)

( * ) Notice: Subject to any disclaimer, the term of this patent is extended or adjusted under 35 U.S.C. 154(b) by 0 days.

(21) Appl. No.: 14/889,675

(22) PCT Filed: May 7, 2014

(86) PCT No.: PCT/JP2014/062269
§ 371 (c)(1),
(2) Date: Nov. 6, 2015

(87) PCT Pub. No.: WO2014/181803
PCT Pub. Date: Nov. 13, 2014

(65) Prior Publication Data
US 2016/0114072 A1   Apr. 28, 2016

(30) Foreign Application Priority Data

May 9, 2013   (JP) ................... 2013-099488
Feb. 28, 2014  (JP) ................... 2014-039750

(51) Int. Cl.
*A01N 25/34*   (2006.01)
*A61L 15/28*   (2006.01)

(52) U.S. Cl.
CPC .................... *A61L 15/28* (2013.01)

(58) Field of Classification Search
None
See application file for complete search history.

(56) References Cited

U.S. PATENT DOCUMENTS

| | | | |
|---|---|---|---|
| 4,579,943 | A | 4/1986 | Kamide et al. |
| 6,214,808 | B1 | 4/2001 | Soe et al. |
| 2004/0039322 | A1 | 2/2004 | Taniguchi et al. |
| 2009/0238849 | A1 | 9/2009 | Iwata et al. |

FOREIGN PATENT DOCUMENTS

| | | |
|---|---|---|
| CN | 101538799 | 9/2009 |
| CN | 103041437 | 4/2013 |
| JP | 3057446 | 6/2000 |
| JP | 2000-256958 | 9/2000 |
| JP | 3114016 | 9/2000 |
| JP | 2002-143210 | 5/2002 |
| JP | 2002-519153 | 7/2002 |
| JP | 2009-256856 | 11/2009 |
| JP | 2011-125695 | 6/2011 |
| WO | WO 93-12275 | 6/1993 |
| WO | WO 00/01425 | 1/2000 |

OTHER PUBLICATIONS

Kyoko (JP2011125695 (A)).*
Junji et al. (JP2009256856 (A)).*
English-language Translation of Written Opinion of the International Searching Authority in Japanese Patent Application No. 2014-062269, mailed Jun. 10, 2014.
English-language International Search Report in Japanese Patent Application No. 2014-062269, mailed Jun. 10, 2014.
Kunihiko Okajima, "Role of Molecular Characteristics on Some Physiological Properties of Cellulose Derivatives", Cellulose Structural and Functional Aspects, Fundamental Research Laboratory of Fibers and Fiber forming Polymers. Asahi Chemical Industry Co., pp. 439-446.
English-language Translations of International Preliminary Report on Patentability in corresponding PCT/JP2014/062269, issued Nov. 10, 2015.
Chinese Office Action in TW Patent Application No. 103116304, dated May 13, 2015.
Supplemental European Search Report in counterpart European Patent Application No. EP 14 79 4171 dated May 10, 2016.
Communication pursuant to Article 94 (3) EPC from European Patent Office in counterpart Patent Application No. EP 14 79 4171 dated Jun. 2, 2016.

* cited by examiner

*Primary Examiner* — Robert A Wax
*Assistant Examiner* — Quanglong Truong
(74) *Attorney, Agent, or Firm* — Finnegan, Henderson, Farabow, Garrett & Dunner L.L.P.

(57) ABSTRACT

The purpose of the present invention is to provide a medical material which, while retaining high liquid absorbency and styptic properties through gelation of CMC, can maintain shape stability even after absorbing a liquid; which has excellent conformance to the skin; and through which the body surface to which it is to be applied is visible. This medical material is a structure comprising regenerated cellulose fibers including carboxymethyl cellulose fibers in which the degree of substitution of the hydroxyl groups in the glucose units making up the cellulose molecule is at least 0.1 but less than 0.5, wherein the medical material is characterized in that the structure has the form of a woven and/or nonwoven fabric, and when the structure is impregnated with physiological saline, the range of the 10% modulus in both the longitudinal direction and the lateral direction of the structure is 0.2 N/50 mm-5.0 N/50 nm, inclusive.

8 Claims, No Drawings

MEDICAL MATERIAL EMPLOYING CARBOXYMETHYL CELLULOSE

TECHNICAL FIELD

The present invention relates to a medical material composed of regenerated cellulose fibers containing carboxymethyl cellulose (hereinafter to also be referred to as CMC).

More particularly, the present invention relates to a medical material used to cover wounds that maintains; shape stability even after absorbing liquid while retaining the highly styptic properties and liquid absorbency of CMC, has superior conformance to the skin, and allows the body surface where it is applied to be visible there through.

BACKGROUND ART

Cellulose oxide, gelatin and microfibrillar collagen are known to be conventional styptic materials used to treat wounds, and are already used in pharmaceutical products and medical equipment. In addition, the following Patent Documents 1 and 2 disclose carboxymethyl cellulose having an action that promotes cellular adhesion. On the other hand, although styptic materials of the prior art protect the surface of a wound by absorbing moisture and swelling to form an adhesive film, excessive absorption of moisture causes the structure thereof to dissolve resulting in the problem of difficulty in retaining shape, and thereby making it difficult to be used at an affected area where there is heavy bleeding such as in the case of using for hemostasis at a puncture site following dialysis, In addition, in the case of a wound, present on human skin, for example, wound protective materials such as surgical dressing or wound covering materials are used so as to protect the wound site, and the following Patent Document 3 describes a soluble wound-healing styptic cellulose fiber in which the degree of substitution of the CMC is 0.5 to less than 1.0. In addition, the following Patent Document 4 describes that, in the case of applying CMC to a wound, there are no residual contaminants having the risk of causing inflammation and so forth at the wound site. However, since CMC having a degree of substitution of 0.5 or more gels excessively rapidly after absorbing liquid, it undergoes a change in form by contracting or dissolving, thereby resulting in problems in terms of use as a wound covering material.

In general, adhesive skin patches for medical use are required to have properties that enable them to conform to movement of the skin and surface irregularities in the skin. Consequently, gauze using cotton or silk was widely used as wound covering materials of the prior art due to its thinness and softness. However, since gauze lacks absorbency and liquid retention, if the amount of exudate from a wound is large, it is unable to suitably absorb the exudate resulting in the occurrence of leakage, and thereby causing soiling of clothing or bed sheets and the like and resulting in an unhygienic situation, while also resulting in the bother of having to frequently replace the gauze in order to prevent leakage of exudate. In addition, although some wound covering materials contain absorbent materials in the manner of foam materials, the presence of an absorbent material resulted in the problem of adhesion of the material to the wound surface, and since this also caused the wound to dry as a result thereof, there was the problem of healing being slower in comparison with healing in a moist state.

PRIOR ART DOCUMENTS

Patent Documents

Patent Document 1: Japanese Patent No. 3057446
Patent Document 2: Japanese Patent No. 3114016
Patent Document 3: Japanese Unexamined Patent Publication No. 2000-256958
Patent Document 4: Japanese Unexamined Patent Publication No. 2002-143210

SUMMARY OF THE INVENTION

Problems to be Solved by the Invention

In consideration of the aforementioned problems associated with the wound styptic materials and wound covering materials of the prior art, an object of the present invention is to provide a medical material that maintains shape stability even after absorbing liquid while retaining the high liquid absorbency and styptic properties attributable to gelation of CMC, has superior conformance to the skin, and allows the body surface where it is applied to be visible there through,

Means for Solving the Problem

As a result of conducting extensive studies and experiments to solve the aforementioned problems, the inventors of the present application found that by controlling the degree of substitution of hydroxyl groups in glucose units that compose cellulose molecules to 0.1 to less than 0.5 and controlling mechanical properties when wet to within a prescribed range, CMC fibers maintain shape stability even after absorbing liquid while retaining high liquid absorbency and styptic properties, and have superior conformance to the skin, thereby leading to completion of the present invention.

Namely, the present invention is as described below.

[1] A medical material in the form of a structure composed of regenerated cellulose fibers containing carboxymethyl cellulose fibers in which the degree of substitution of hydroxyl groups in glucose units that compose the cellulose molecules is 0.1 to less than 0.5, wherein the structure has the form of a woven and/or nonwoven fabric, and when the structure is impregnated with physiological saline, the range of the 10% modulus of the structure in both the longitudinal direction and lateral direction is 0.2 N/50 mm to 5.0 N/50 mm.

[2] The medical material described in [1] above, wherein the value obtained by dividing the 10% modulus in the longitudinal direction by the 10% modulus in the lateral direction is 0.5 to 5.0.

[3] The medical material described in [1] or [2] above, wherein the lightness index of the structure is 9.0 to 30.0.

[4] The medical material described in any of [1] to [3] above, wherein the liquid absorbency of the structure is 5.0 g/100 cm$^2$ to 40.0 g/100 cm$^2$.

[5] The medical material described in any of [1] to [4] above, wherein the regenerated cellulose fibers are continuous long fibers.

[6] A wound covering material that uses the medical material described in any of [1] to [5] above.

[7] A wound styptic material that uses the medical material described in any of [1] to [5] above.

[8] An adhesive bandage that uses the medical material described in any of [1] to [5] above.

Effects of the Invention

The medical material according to the present invention maintains shape stability even after absorbing a liquid while retaining high liquid absorbency and styptic properties, has superior conformance to the skin, and can be used at almost any site on the body surface.

EMBODIMENTS FOR CARRYING OUT THE INVENTION

The following provides a detailed explanation of embodiments of the present invention.

In order to substitute carboxymethyl groups for hydroxyl groups in glucose units composing cellulose molecules, cellulose fibers are converted to alkaline cellulose in the presence of base followed by reacting in a sodium monochloroacetate solution containing alcohol. Here, it is important to regulate the reaction temperature to 30° C. to 50° C. in order to control the degree of substitution, and at a temperature below 30° C., the reaction rate is excessively slow, while at a temperature above 50° C., side reactions occur and reaction efficiency decreases. Although the degree of substitution can be controlled by carrying out the reaction for 2 hours to 10 hours while maintaining a stirred state, the bath ratio between the reaction solution and cellulose fibers is also an important element for controlling the degree of substitution. Reaction conditions can be suitably modified while considering such factors as production cost and the like.

In the present invention, the range of the degree of substitution of CMC is important, and if the degree of substitution reaches 0.5 or more, solubility becomes high resulting in the problem, of the CMC structure dissolving and being unable to retain its shape in the case of having contacted, an exudate. On the other hand, if the degree of substitution is less than 0.1, the sense of gelation is unable to be retained and styptic and wound protective functions are unable to be adequately demonstrated.

Although the terminals of carboxymethyl groups form sodium salts following completion of the reaction, they may remain in the form of sodium salts or may be treated with acid to obtain a proton form or may be an intermediate thereof.

There are no particular limitations on the fiber material of the regenerated cellulose fibers used in the present invention, and known fibers are used, examples of which include cuprammonium, rayon, viscose rayon and Lyoceli (Tencel) ®. The single yarn fineness of fibers composing a nonwoven fabric is preferably about 0.1 dtex to 3 dtex, in addition, since a nonwoven fabric to which a binder has been, added has a slow solution penetration rate and there is concern over elution of binder components, a binder-free nonwoven fabric is used preferably.

A nonwoven fabric as referred to in the present invention may be that in the form of a sheet in which the fibers are not woven but simply entangled, the fibers may be short fibers or long fibers, and the fibers may be flocked. In addition, the manner of entanglement includes that in which fibers are adhered by thermomechanical, water flow or chemical action. A continuous long fiber nonwoven fabric is preferable since short fibers do not disintegrate during carboxymethylation.

The medical material used in the present invention preferably contains 91% or more of the aforementioned regenerated cellulose fibers. If the content thereof is less than 91%, the function of the carboxymethyl cellulose fibers is inadequate, and their function as a medical material is not adequately demonstrated.

The medical material of the present invention is required to demonstrate shape stability when wet. Shape stability as referred to here refers to the 10% modulus in both the longitudinal and lateral directions of a nonwoven fabric being within the range of 0.2 N/50 mm to 5.0 N/50 mm when the nonwoven fabric is impregnated with physiological, saline, and this simulates stability of the CMC sheet when it has absorbed liquid on a wound surface.

The range of the 10% modulus in both the longitudinal and lateral directions is more preferably 0.5 N/50 mm to 2.5 N/50 mm. If the 10% modulus is less than 0.2 N/50 mm, the sheet becomes weak and is torn easily, thereby resulting in the problem of being unable to maintain the periodical state of wound healing. If the 10% modulus exceeds 5.0 N/50 mm, the medical material is unable to conform, to the skin resulting in the problem of poor adhesion. In addition, an excessively large difference between the ratios of the 10% modulus in the longitudinal and lateral directions also presents problems. More specifically, since the problem of warping or increased susceptibility to peeling of the sheet occurs during the course of having absorbed body fluid on the wound surface followed by evaporation of moisture over time, the sheet is required to have post-drying linearity. In order to demonstrate post-drying linearity, the value obtained by dividing the 10% modulus in the longitudinal direction by the 10% modulus in the lateral direction is preferably 0.5 to 5.0, more preferably 0.6 to 4.0 and even more preferably 0.7 to 3.0.

In order for the medical, material of the present invention to demonstrate shape stability, properties of the nonwoven fabric prior to the CMC reaction are preferably set to a suitable range. More specifically, properties of the nonwoven fabric are as follows:

(i) fibers are preferably entangled so that the fibers do not fall, out;

(ii) the ratio between tensile strength of the nonwoven fabric in the wet state after entanglement in the longitudinal direction (direction in which the nonwoven fabric proceeds through production equipment) and that in the lateral direction (direction perpendicular to the direction in which the nonwoven fabric proceeds through production, equipment) is preferably within the range of 0.5 to 7.0, more preferably 1.0 to 6.0 and even more preferably 1.0 to 4.5;

(iii) the nonwoven fabric is preferably in the form of a sheet having a basis weight of 20 g/m$^2$ or more, and although there are no particular limitations thereon, is more preferably in the form of a sheet having a basis weight of 150 g/m$^2$ or less in terms of handling, while the basis weight following CMC conversion is preferably 30 g/m$^2$ to 200 g/m$^2$; and, (iv) the thickness of the sheet is preferably 0.1 mm or more.

Fibers are observed to fail out during CMC conversion and desired effects cannot be obtained unless the fibers are entangled. In addition, if the tensile strength ratio in the wet state between the longitudinal and lateral directions following entanglement is outside the range of 0.5 to 7.0, balance between the longitudinal and lateral directions following CMC conversion becomes poor, thereby causing the medical material, to shrink in one of the directions when wet and preventing it from adequately covering a wound. A sheet of the medical material of the present invention is required, to not shrink and exhibit little dimensional change even if wet. Dimensional change as measured according to a method to be subsequently described is preferably −10% to +20% and more preferably −5% to +5%. If the dimensional change is less than −10%, the area of the sheet, is inadequate thereby preventing the sheet from adequately covering a wound. In addition, if dimensional change exceeds +20%, the fibers become untangled resulting in the problem of the sheet tearing apart. In addition, if the basis weight of the nonwoven fabric is less than 20 g/m$^2$, the amount of CMC fibers relative to the wound surface becomes low, thereby preventing the wound surface from being protected after absorbing liquid. If the basis weight after CMC conversion is less than 30 g/m$^2$, the amount of CMC fibers relative to the wound surface becomes low, thereby preventing wound exudate from being adequately absorbed. On the other hand, in the case the basis weight exceeds 200 g/m$^2$, the amount of CMC fibers becomes more than what is necessary, thereby resulting in increased costs.

In addition, in the prior art, since stress to which a nonwoven fabric is subjected differs between the longitudinal direction, of the nonwoven fabric (direction in which the nonwoven fabric proceeds through production equipment) and lateral direction of the nonwoven fabric (direction perpendicular to the direction in which the nonwoven fabric proceeds through production equipment), a large strength ratio occurred between the longitudinal and lateral directions of the nonwoven fabric after entangling. For example, in the case of water flow entanglement, although a method has been used, in which columnar flow is contacted with a nonwoven fabric while oscillating the nonwoven fabric in the lateral direction such as by oscillating the columnar flow in the longitudinal direction, this method was inadequate. Making the strength ratio between the longitudinal and lateral directions of a nonwoven fabric in the wet state to be within the range of 0.5 to 4.5 can be achieved by placing the nonwoven fabric on a net and subjecting to water flow entanglement, thereby temporarily transferring the pattern of the net to the nonwoven fabric, followed by again placing a mesh that is finer than that used the first time on the nonwoven fabric and again subjecting to water flow entanglement. This is presumed to be due to anisotropy in the longitudinal and lateral directions being alleviated by realigning the fibers twice.

An example of a preferable nonwoven fabric composed, of regenerated cellulose fibers is a nonwoven fabric composed of continuous long fibers of cuprammonium rayon that is formed to have porosity by entangling a large number of continuous filaments without using an adhesive. Since this cellulose nonwoven fabric has a high degree of polymerization of about 500, it has high tensile strength, ample fillability, favorable texture, demonstrates little decrease in tensile strength even if the cellulose nonwoven fabric is carboxymethylated, and is resistant to structural failure and significant decreases in flexibility, thereby making it preferable. There are regenerated cellulose fiber non-woven fabrics composed of other short fibers that use cellulose materials having a low degree of polymerization, and in contrast to the fibers easily degrading when the degree of substitution increases thereby requiring the degree of substitution to be made to be as low as possible since these nonwoven fabrics are composed of short fibers, since the use of continuous filaments of cuprammonium rayon permits a high degree of substitution and since they are composed of continuous long fibers, there is the advantage of being resistant to disintegration even at comparatively high degrees of substitution. Fiber fineness is preferably 0.1 dtex to 3.0 dtex and more preferably 0.5 dtex to 2.5 dtex. If fineness exceeds 3.0 dtex, fiber diameter becomes excessively large and the reaction does not proceed uniformly in the direction of the fiber axis, while if fineness is less than 0.1 dtex, the fibers are excessively narrow, resulting in the problem of the fibers dissolving during the reaction.

The medical material of the present invention may be affixed directly to an affected area or may be used in combination with ordinary gauze. In addition, there are no particular limitations on the shape of the medical material of the present invention, and can be adjusted as desired to match the size of the wound.

As was previously described, the degree substitution of the CMC of the present invention is preferably 0.1 to less than 0.5 and more preferably 0.2 to less than 0.5. If the degree of substitution is 0.5 or more, solubility increases and the CMC structure ends up dissolving in the case of having contacted an exudate, thereby resulting in the problem of being unable to retain its shape. On the other hand, if the degree of substitution is less than 0.1, the sense of gelation is unable to be retained and styptic and wound protective functions are unable to be adequately demonstrated.

The sheet-like structure of the present invention is such that liquid absorbency as measured according to a method to be subsequently described is preferably 5.0 g/100 cm to 40.0 g/100 cm, more preferably 6.0 g/100 cm to 35.0 g/100 cm and even more preferably 8.0 g/100 cm to 35.0 g/100 cm. If liquid absorbency is less than 5.0 g/100 cm, retention of body fluid becomes poor, while if liquid absorbency exceeds 40.0 g/100 cm, the amount of body fluid increases excessively, thereby preventing the wound from being maintained in a wet state.

In addition, lightness index as measured according to a method to be subsequently described is preferably 9.0 to 30.0. Lightness index represents a value measured with a colorimeter according to the L*a*b* color system, and in the case this value is 30.0 or less, the condition of a wound can be confirmed even if the wound is covered with the sheet, thereby making this useful. If the lightness index exceeds 30.0, wound visibility is insufficient. On the other hand, if the lightness index is 9.0 or more, transparency is adequate, while even if the lightness index is less than 9.0, differences in visibility cannot be detected.

Radiation sterilization is preferable for the method used to sterilize the medical material of the present invention, and although sterilization with gamma rays or an electron beam is more preferable, the medical material of the present invention may also be sterilized by gas sterilization, including that using ethylene oxide gas (EOG).

Although the following provides descriptions of methods used to evaluate basis weight, thickness and tensile strength, these parameters are measured using fibers prior to the CMC reaction.

[Measurement of Nonwoven Fabric Basis Weight]

The basis weight (g/m$^2$) of natural or regenerated cellulose fibers composing the medical material of the present invention was measured according to the method indicated below. After drying a nonwoven fabric of cellulose-based fibers having an area of 0.05 m$^2$ or more for 1 hour at 105° C., the weight of the nonwoven fabric in the dryer was measured, and that weight was multiplied by the standard moisture content of cellulose of 11.0% to determine basis weight in terms of the weight (g) per 1 m$^2$ of nonwoven fabric.

[Measurement of Thickness]

Thickness of the natural or regenerated cellulose fibers composing the medical, material of the present invention was measured according to the method indicated below. The nonwoven fabric was measured, using a load of 1.95 kPa with a thickness tester complying with JIS-L1096.

[Tensile Strength]

Wet tensile strength (N/50 mm) was measured in compliance with JIS-L1096 (1993 revised edition) (while using pure water for the solution).

Although the following indicates measurement methods used to evaluate the degree of substitution of CMC, basis weight, liquid absorbency, lightness index, visibility, 10% modulus, conformability, post-drying linearity, styptic properties (styptic action) and dimensional change, these were measured using materials following the CMC reaction.

[Measurement of CMC Degree of Substitution]

The degree of substitution of CMC contained in natural or regenerated cellulose fibers composing the medical material of the present invention can be measured according to the method indicated below.

1 g of carboxymethylated fibers are finely chopped and placed in a flask followed by the addition of 25 mL of nitric acid-methanol (mixed liquid consisting of 10 mL of nitric acid and 100 mL of methanol) and stirring for 1 hour. Next, the sample is collected by subjecting to suction filtration with a glass filter (G3) followed by washing with 120 mL of an 800 g/L aqueous methanol solution (mixture of 100 mL of methanol and 20 mL of water, 40 mL×3 washings), finally washing with 25 mL of 100% methanol, subjecting to suction filtration and allowing to air dry for one day. After drying the sample for 2 hours at 105° C., 0.2 g of sample in the H form are accurately weighed out followed by the addition of 8 mL of an 800 g/L methanol, solution and 20 mL of a 0.1 mol/L aqueous sodium, hydroxide solution and stirring for 30 minutes to convert the H-form sample to the Na form. An excess of sodium hydroxide is then titrated with 0.05 mol/L sulfuric acid having a known normality using phenolphthalein for the indicator. In addition, a blank test (same test carried out on non-carboxymethylated fibers) is carried out using the same method. The equation used to calculate degree of substitution is as follows:

$C$=sulfuric acid concentration×{(amount titrated during blank test−amount titrated when using sample)/sample weight}

Degree of substitution=$162C/(1-58C)$ (wherein, C represents the amount of NaOH (mol) required to convert 1 g of sample to the Na form).

[Measurement of CMC Basis Weight]

The basis weight (g/m$^2$) of natural or regenerated cellulose fibers composing the medical material of the present invention was measured according to the following method. A CMC sheet having an area of 0.05 m$^2$ or more was accurately weighed with an electronic balance and that weight was divided by the area to determine the basis weight in terms of the weight (g) per 1 m$^2$ of CMC.

[Measurement of Liquid Absorbency]

Liquid absorbency of the medical material of the present invention can be measured according to the method indicated below.

Absorption, capacity when allowed to swell freely was measured in compliance with EN13726-1.

[Measurement of Lightness Index]

Lightness index of the medical, material, of the present invention can be measured according to the method indicated below.

A sample measuring 5 cm×5 cm is collected and the weight thereof is measured with an electronic pan balance. The sample is then placed on a glass plate and impregnated with an amount of physiological saline equal to 15 times the weight of the sample followed by measuring lightness index using the SM-T S&M Color Meter (Suga Test Instruments Co., Ltd,) according to the L*a*b* color system. A standard black plate was placed in the background at that time. With respect to L* representing lightness, the case of placing the sample on the glass plate was defined as L*(sample), the case of measuring only the glass plate without placing the sample thereon was defined as L*(blank), and ΔL* was defined as L*(sample)−L*(blank). Since a standard black plate was used for the background, the value of ΔL* becomes smaller as transparency becomes higher.

[Visibility]

Visibility of the medical material of the present invention can be assessed according to the method indicated below.

A sample measuring 2 cm×2 cm is collected and the weight of the sample is measured with an electronic pan balance. The sample is immersed in an amount of physiological saline equal to 15 times the weight of the sample, and visibility of the surface portion of an adherend through the sheet was evaluated to one of three levels consisting of visible (A), barely visible (B) and not visible (C). A seal having the word "evaluation" written on a white background was used for the adherend.

[Measurement of 10% Modulus]

10% modulus (N/50 Kim) was measured in compliance with JIS-L1096 (1999 revised edition. Here, physiological saline was used for the solution.

[Evaluation of Conformability]

The conformability of the medical material of the present invention can be evaluated according to the method indicated below.

A sample measuring 5 cm×3 cm is collected and the weight of the sample is measured with an electronic pan balance. After immersing the sample in an amount of physiological saline equal to 15 times the weight of the sample, the sample was affixed, to the back of the hand followed by opening and closing the hand ten times. Shape was evaluated according to the evaluation criteria indicated below.

A: The sheet can be lifted up while retaining its shape even after impregnating with physiological, saline, and the sheet is adhered to the skin even after opening and closing the hand ten times after having been affixed to the skin.

B: Although the sheet can be lifted up while retaining its shape even after impregnating with physiological saline, when the hand is opened and closed ten times after affixing to the skin, the sheet separates from the back of the hand.

C: The sheet dissolves and cannot be lifted up while retaining its shape after impregnating with physiological saline.

[Evaluation of Post-Drying Linearity]

Evaluation of post-drying linearity of the medical material of the present invention can be assessed according to the method indicated below.

A sample measuring 5 cm×5 cm is collected and the weight of the sample is measured with an electronic pan balance. After immersing the sample in an amount of physiological saline equal to 15 times the weight of the sample, the sample is transferred to a Petri dish having an inner diameter of 85 mm, and after drying for 12 hours in a not air dryer at 37° C., warping of the sheet is observed. The case of the edges of the sheet rising 3 mm or more from the Petri dish was evaluated as an absence of post-drying linearity and assessed as C, while the case of the edges of the sheet, rising by less than 3 mm was evaluated as the presence of post-drying linearity and assessed as A.

[Evaluation of Styptic Properties]

Styptic properties (styptic action) of the wound styptic material of the present invention can be confirmed according to the method indicated below.

A rat is laparotomized after anesthetizing with pentobarbital sodium and an incision is made in the surface of the left external lobe of the liver over a diameter of 8 mm and to a depth of 1 to 2 mm. After confirming bleeding from the incised wound, a sample measuring 15 mm on a side is affixed and after applying pressure for 1 minute, the presence of bleeding from the wound surface is observed and the number of cases that exhibited bleeding among a total of six cases is recorded.

[Dimensional Change]

Evaluation of dimensional change of the medical material of the present invention can be assessed according to the method indicated below.

After collecting a sample measuring 5 cm×5 cm and immersing the sample in an amount of physiological saline equal to 15 times the weight of the sample, the rate of change (%) from the original area (25 cm$^2$) was determined. Cases in which area increased were represented with a positive value, while oases in which area decreased were represented with a negative value.

Rate of change (%)=(area after moisture absorption−25)/25×100

EXAMPLES

Although the following provides a detailed explanation of the medical material of the present invention, using examples thereof, the present invention is not limited by these examples.

Example 1

After spinning and refining cupra nonwoven fabric according to known methods, the nonwoven fabric was subjected to water flow entanglement with a water needle by applying pressure of 15 kg/cm$^2$ on a 20 mesh net (having 20 openings per inch). Next, after temporarily stripping off the nonwoven fabric with a stripping roller, the nonwoven fabric was again, subjected to water flow entanglement with a water needle by applying a pressure of 20 kg/cm$^2$ on a 30 mesh net in the next step. Next, after drying by hot air drying at 120° C., the nonwoven fabric was wound up with a winder to obtain a regenerated, cellulose continuous long fiber non-woven fabric. Furthermore, spinning conditions at this time were adjusted so that the nonwoven fabric had a basis weight of 80 g/m$^2$ and thickness of 0.41 mm at a line speed of 20 m/min. Longitudinal strength in the wet state at this time was 27.1 N/50 mm, strength in the lateral direction was 21.3 N/50 mm, and the tensile strength ratio (longitudinal strength/lateral strength) was 1.27. Next, 9.0 g of the resulting regenerated cellulose continuous long fiber nonwoven fabric (cupra nonwoven fabric) (size: 10 cm×75.0 cm, basis weight: 80 g/m$^2$) were placed in a reaction vessel followed by the addition of 172 mL of an aqueous ethanol solution, containing sodium hydroxide (3.3 mol/L sodium hydroxide, 50% by volume aqueous ethanol solution) and allowing to stand undisturbed at room temperature for 30 minutes. The nonwoven fabric was taken out of the reaction vessel and placed in 300 mL of preliminarily prepared aqueous ethanol solution containing sodium monochloroacetate (0.35 mol/L sodium monochloroacetate, 0.33 mol/L sodium hydroxide, 80% by volume ethanol) followed by stirring for 3 hours at 30° C. After adjusting the pH to 6.0 to 8.0 with a 1% by weight aqueous acetic acid solution diluted with 80% by volume ethanol, the nonwoven fabric was washed twice with an 80% by volume aqueous ethanol solution and subjected to alcohol substitution with 100% ethanol. Subsequently, the nonwoven fabric was dried to obtain a carboxymethylated nonwoven fabric.

Example 2

A reaction was carried out under the same conditions as Example 1 with the exception of making the temperature of the reaction between a regenerated cellulose continuous long fiber nonwoven fabric (cupra nonwoven fabric) obtained, using the same method as Example 1 and the aqueous sodium monochloroacetate solution 45° C.

Example 3

A regenerated, cellulose continuous long fiber nonwoven fabric: (cupra nonwoven fabric) was obtained using the same method as Example 1 with the exception of adjusting spinning conditions so that the nonwoven fabric had a basis weight of 38 g/m$^2$ and thickness of 0.31 mm at a line speed of 25 m/min. A reaction was carried out under the same conditions as Example 1 with the exception of making the duration of the reaction between the resulting nonwoven fabric and the aqueous sodium monochloroacetate solution 2 hours.

Example 4

A regenerated cellulose continuous long fiber nonwoven fabric (cupra nonwoven fabric) was obtained using the same method as Example 1 with the exception of adjusting spinning conditions so that the nonwoven fabric had a basis weight of 101 g/m$^2$ and thickness of 0.43 mm at a line speed of 16 m/min. A reaction was carried out under the same conditions as Example 1 with the exception of making the duration of the reaction between the resulting nonwoven fabric and the aqueous sodium monochloroacetate solution 2 hours.

Example 5

Instead of a regenerated cellulose continuous long fiber nonwoven fabric (cupra nonwoven fabric), a woven fabric obtained by combining yarn, in which 1.8 dtex regenerated cellulose fibers (cupra fibers) were converged to 66 dtx and 84 dtx, was reacted with the aqueous sodium monochloroacetate solution under the same conditions as Example 1.

Example 6

Instead of a regenerated cellulose continuous long fiber nonwoven fabric (cupra nonwoven fabric), a rayon-based fiber nonwoven fabric (short fiber nonwoven fabric, basis weight: 60 g/m$^2$) was used to react with the aqueous sodium monochloroacetate solution under the same conditions as Example 1.

Example 7

A mixed nonwoven fabric was obtained by mixing 92% by weight of 55 dtex regenerated cellulose fibers and 8% by weight of polyethylene terephthalate short fibers and subjecting to water flow entanglement. The resulting nonwoven fabric was reacted under the same conditions as Example 5.

Example 8

A reaction was carried out under the same conditions as Example 1 with the exception of using a Lyocell-based fiber nonwoven fabric (basis weight: 60 g/m$^2$) instead, of a regenerated cellulose continuous long fiber nonwoven fabric (cupra nonwoven fabric) and making the temperature of the reaction with the aqueous sodium monochloroacetate solution 40° C.

Comparative Example 1

A regenerated cellulose continuous long fiber nonwoven fabric (cupra nonwoven fabric) obtained using the same method as Example 1 that was not subjected to carboxymethylation was used in Comparative Example 1.

Comparative Example 2

A reaction was carried out under the same conditions as Example 1 with the exception of making the temperature of the reaction between a regenerated cellulose continuous long fiber nonwoven fabric (cupra nonwoven fabric) obtained using the same method as Example 1 and the aqueous sodium monochloroacetate solution 50° C. and making the reaction time 6 hours.

Comparative Example 3

A regenerated cellulose continuous long fiber nonwoven fabric (cupra nonwoven fabric) was obtained using the same method as Example 1 with the exception of carrying out water flow entanglement only once prior to stripping with the stripping roller and adjusting the spinning conditions so that the nonwoven fabric had a basis weight of 38 g/m$^2$ and thickness of 0.30 mm at a line speed of 25 m/min. A reaction was carried out under the same conditions as Example 1 with the exception of making the duration of the reaction between the resulting nonwoven fabric and the aqueous sodium monochloroacetate solution 2 hours.

Comparative Example 4

A reaction was carried out under the same conditions as Example 1 with the exception of subjecting fibers having a dry weight of 100 g/m$^2$ which were formed from solvent-spun cellulose filaments spun using N,N-dimethylformamide for the solvent, to water flow entanglement with a water needle by applying a pressure of 15 kg/end.

TABLE 1

| | | Ex. 1 | Ex. 2 | Ex. 3 | Ex. 4 | Ex. 5 | Ex. 6 | Ex. 7 |
|---|---|---|---|---|---|---|---|---|
| Fiber material | | Cupra nonwoven fabric | Cupra nonwoven fabric | Cupra nonwoven fabric | Cupra nonwoven fabric | Cupra nonwoven fabric | Rayon nonwoven fabric | Cupra/PET compound fabric |
| Before CMC reaction | Thickness (mm) | 0.41 | 0.38 | 0.31 | 0.43 | 0.21 | 0.20 | 0.25 |
| | Basis weight (g/m$^2$) | 80.2 | 78.9 | 38.4 | 101.3 | 63.1 | 60.1 | 65 |
| | Tensile strength (N/50 mm) Long. | 27.1 | 24.2 | 13.9 | 28.9 | 175 | 67.1 | 225 |
| | Tensile strength (N/50 mm) Lat. | 21.3 | 19.5 | 11.4 | 15.6 | 166 | 52.2 | 201 |
| | Strength ratio (long/lat) | 1.27 | 1.24 | 1.22 | 1.85 | 1.05 | 1.29 | 1.12 |
| Reaction time (h) | | 3 | 3 | 2 | 2 | 3 | 3 | 3 |
| Reaction temp. (° C.) | | 30 | 45 | 30 | 30 | 30 | 30 | 30 |
| After CMC reaction | Degree of substitution (—) | 0.23 | 0.49 | 0.11 | 0.12 | 0.23 | 0.19 | 0.20 |
| | Basis weight (g/m$^2$) | 103.6 | 115.2 | 50.3 | 101.3 | 120.9 | 75.4 | 80.3 |
| | Liquid absorbency (g/100 cm$^2$) | 8.61 | 32.6 | 6.58 | 9.62 | 6.08 | 8.5 | 5.85 |
| | Lightness index (—) | 23.5 | 9.6 | 25.9 | 27.3 | 28.3 | 28.6 | 29.8 |
| | 10% modulus (N/50 mm) Long. | 2.10 | 0.65 | 2.00 | 3.20 | 1.86 | 0.65 | 3.25 |
| | 10% modulus (N/50 mm) Lat. | 1.34 | 0.51 | 1.35 | 1.87 | 2.07 | 0.60 | 3.11 |
| | 10% modulus (N/50 mm) Long/Lat | 1.57 | 1.27 | 1.48 | 1.71 | 0.89 | 1.08 | 1.04 |
| | Visibility | A | A | A | A | B | B | B |
| | Conformability | A | A | A | A | A | A | A |
| | Post-drying linearity | A | A | A | A | A | A | A |
| | Dimensional change (%) | −2.3 | −4.7 | −1.6 | −1.4 | −2.6 | −4.6 | −0.5 |
| | Styptic properties | 6/6 | 6/6 | 6/6 | 6/6 | 6/6 | 6/6 | 5/6 |

| | | Ex. 8 | Comp. Ex. 1 | Comp. Ex. 2 | Comp. Ex. 3 | Comp. Ex. 4 |
|---|---|---|---|---|---|---|
| Fiber material | | Lyocell nonwoven fabric | Cupra nonwoven fabric | Cupra nonwoven fabric | Cupra nonwoven fabric | Lyocell nonwoven fabric |
| Before CMC reaction | Thickness (mm) | 0.40 | 0.48 | 0.41 | 0.30 | 0.48 |
| | Basis weight (g/m$^2$) | 60.4 | 80.5 | 78.6 | 37.8 | 100.2 |
| | Tensile strength (N/50 mm) Long. | 50.1 | 25.3 | 26.0 | 53.6 | 44.5 |
| | Tensile strength (N/50 mm) Lat. | 32.3 | 18.2 | 20.4 | 7.6 | 8.9 |
| | Strength ratio (long/lat) | 1.55 | 1.39 | 1.27 | 7.05 | 5.00 |
| Reaction time (h) | | 3 | — | 6 | 2 | 3 |
| Reaction temp. (° C.) | | 40 | — | 50 | 30 | 30 |
| After CMC reaction | Degree of substitution (—) | 0.30 | 0.00 | 0.61 | 0.12 | 0.11 |

TABLE 1-continued

|  |  |  |  |  |  |  |
|---|---|---|---|---|---|---|
| Basis weight (g/m²) |  | 79.4 | 80.5 | 116.1 | 50.1 | 128.8 |
| Liquid absorbency (g/100 cm²) |  | 8.3 | 5.92 | Unmeasurable | 6.35 | 6.3 |
| Lightness index (—) |  | 27.4 | 33.5 | 8.3 | 25.6 | 35 |
| 10% modulus (N/50 mm) | Long. | 0.89 | 25.3 | Unmeasurable | 5.01 | 4.5 |
|  | Lat. | 0.95 | 17.7 | Unmeasurable | 0.19 | 0.15 |
|  | Long/Lat | 0.93 | 1.42 | Unmeasurable | 26.4 | 30 |
| Visibility |  | B | C | A | A | B |
| Conformability |  | A | B | C | C | C |
| Post-drying linearity |  | A | A | A | C | C |
| Dimensional change (%) |  | −4.9 | 0.9 | −10.6 | −20.1 | −21.9 |
| Styptic properties |  | 6/6 | 0/6 | 2/6 | 2/6 | 1/6 |

Comparative Example 1 had poor visibility and styptic properties while Comparative Example 2 had poor shape stability. Comparative Example 2 dissolved in physiological saline, modulus was unable to be measured and shape stability was poor. Although the lateral modulus of Comparative Examples 3 and 4 was excessively low, longitudinal modulus was excessively high, thereby resulting in poor shape stability, and this was determined to unable to be used as a medical material.

INDUSTRIAL APPLICABILITY

Since the medical material of the present invention maintains shape stability even after absorbing liquid while retaining high styptic properties and liquid absorbency attributable to CMC, and has superior conformance to the skin, it can be preferably used on wounds having an irregular surface, and can be preferably used either alone or in combination with, gauze as a wound covering material, wound, styptic agent or adhesive bandage.

The invention claimed is:

1. A medical material in the form of a structure composed of regenerated cellulose fibers containing carboxymethyl cellulose fibers in which the degree of substitution of hydroxyl groups in glucose units that compose the cellulose molecules is 0.1 to less than 0.5, wherein the structure has the form of a woven and/or nonwoven fabric, and when the structure is impregnated with physiological saline, the range of the 10% modulus of the structure in both the longitudinal direction and lateral direction is 0.2 N/50 mm to 5.0 N/50 mm.

2. The medical material according to claim 1, wherein the value obtained by dividing the 10% modulus in the longitudinal direction by the 10% modulus in the lateral direction is 0.5 to 5.0.

3. The medical material according to claim 1 or 2, wherein the lightness index of the structure is 9.0 to 30.0.

4. The medical material according to claim 1 or 2, wherein the liquid absorbency of the structure is 5.0 g/100 cm² to 40.0 g/100 cm².

5. The medical material according to claim 1 or 2, wherein the regenerated cellulose fibers are continuous long fibers.

6. A wound covering material that uses the medical material according to claim 1 or 2.

7. A wound styptic material that uses the medical material according to claim 1 or 2.

8. An adhesive bandage that uses the medical material according to claim 1 or 2.

* * * * *